US010064668B2

(12) United States Patent
Johnston, Jr. et al.

(10) Patent No.: US 10,064,668 B2
(45) Date of Patent: Sep. 4, 2018

(54) BONE PLATE LOCKING CANNULA AND DRILL GUIDE ASSEMBLY

(71) Applicants: Thomas S. Johnston, Jr., Jacksonville, FL (US); Jennifer C. Pinto, Jacksonville, FL (US)

(72) Inventors: Thomas S. Johnston, Jr., Jacksonville, FL (US); Jennifer C. Pinto, Jacksonville, FL (US)

(73) Assignee: KLS-MARTIN, L.P., Jacksonville, FL (US)

( * ) Notice: Subject to any disclaimer, the term of this patent is extended or adjusted under 35 U.S.C. 154(b) by 282 days.

(21) Appl. No.: 14/880,337

(22) Filed: Oct. 12, 2015

(65) Prior Publication Data
US 2016/0235451 A1    Aug. 18, 2016

Related U.S. Application Data

(60) Provisional application No. 62/115,990, filed on Feb. 13, 2015.

(51) Int. Cl.
*A61B 17/80* (2006.01)
*A61B 17/17* (2006.01)
*A61B 17/86* (2006.01)

(52) U.S. Cl.
CPC ........ *A61B 17/808* (2013.01); *A61B 17/1728* (2013.01); *A61B 17/80* (2013.01); *A61B 17/8047* (2013.01); *A61B 17/8052* (2013.01); *A61B 17/8085* (2013.01); *A61B 17/8057* (2013.01); *A61B 17/8605* (2013.01)

(58) Field of Classification Search
CPC ...................... A61B 17/80–17/8095
See application file for complete search history.

(56) References Cited

U.S. PATENT DOCUMENTS

| 5,364,399 | A | * | 11/1994 | Lowery | .............. | A61B 17/1728 |
| | | | | | | 606/286 |
| 6,102,951 | A | * | 8/2000 | Sutter | .................... | A61B 17/17 |
| | | | | | | 606/304 |
| 6,436,103 | B1 | * | 8/2002 | Suddaby | ............ | A61B 17/1728 |
| | | | | | | 606/281 |

(Continued)

FOREIGN PATENT DOCUMENTS

WO    WO 2014/096905    *    6/2014    ............. A61B 17/80

*Primary Examiner* — Zade Coley
(74) *Attorney, Agent, or Firm* — Thomas C. Saitta

(57) ABSTRACT

A bone plate locking cannula and drill guide assembly having a locking cannula detachably mountable onto screw-receiving apertures of a bone plate and a drill guide received within the locking cannula such that pilot holes are drilled through the apertures into bone at the proper angle to receive bone screws. The screw receiving apertures have a proximal bore of greater diameter than a distal bore, and the proximal bore is provided with internal threading to mate with external threading located on the distal end of the locking cannula. The bone screws are inserted through the locking cannula after removal of the drill guide and fastened into the bone to secure the bone plate in position without having to remove the locking cannulas from the bone plate, the internal diameter of the locking cannula bore being greater than the maximum diameter of the screw heads. The locking cannula is detached from the bone plate after the bone plate has been secured in place on the bone.

15 Claims, 6 Drawing Sheets

(56) References Cited

U.S. PATENT DOCUMENTS

| | | | |
|---|---|---|---|
| 7,935,126 B2* | 5/2011 | Orbay | A61B 17/1728 606/101 |
| 8,241,338 B2* | 8/2012 | Castaneda | A61B 17/1728 606/280 |
| 8,398,685 B2* | 3/2013 | McGarity | A61B 17/1728 606/281 |
| 8,545,540 B2* | 10/2013 | Castaneda | A61B 17/1728 606/291 |
| 8,674,762 B2 | 3/2014 | Templ et al. | |
| 8,834,537 B2* | 9/2014 | Castaneda | A61B 17/1728 606/280 |
| 8,858,562 B2 | 10/2014 | Orbay et al. | |
| 2005/0234467 A1* | 10/2005 | Rains | A61B 17/1728 606/96 |
| 2006/0004361 A1 | 1/2006 | Haycek et al. | |
| 2008/0140130 A1* | 6/2008 | Chan | A61B 17/1728 606/280 |
| 2010/0057138 A1* | 3/2010 | Murner | A61B 17/1728 606/308 |
| 2012/0089192 A1* | 4/2012 | Biedermann | A61B 17/1728 606/280 |
| 2014/0180345 A1* | 6/2014 | Chan | A61B 17/1728 606/291 |

\* cited by examiner

BONE PLATE LOCKING CANNULA AND DRILL GUIDE ASSEMBLY

This application claims the benefit of U.S. Provisional Patent Application Ser. No. 62/115,990, filed Feb. 13, 2015.

BACKGROUND OF THE INVENTION

This invention relates in general to rigid metal plates adapted for attachment to bones (typically referred to as bone plates) with screw-type fasteners (typically referred to as bone screws) and to guide devices used to properly align a drill to create the bore in the bone that will receive the screw-type fastener inserted through an aperture in the bone plate. The invention also relates to tubular drill guides that are used to properly align a drill bit when a pilot hole is being drilled into the bone.

With many bone fractures or surgical osteotomies it is necessary to secure the bone segments in a fixed, rigid manner such that natural healing may occur. A common way to accomplish this is to provide a rigid metal plate shaped and sized as required to correspond to the bone or bones being secured, the rigid plate having apertures to receive bone screws, the bone screws being inserted through the plate and into the bone to secure the plate to bone and thereby prevent relative movement of the bone segments during the healing process. Additionally, bone plates are utilized in distraction procedures—the bone plates being affixed to opposing bone segments that are slowly separated by a distraction mechanism in known manner to lengthen the bone by osteogenesis. In most cases it is desirable or even necessary to first drill a pilot hole or bore into the bone at the location for each screw so as to prevent fracturing or splintering of the bone when the bone screw is inserted. Given the need to reduce undesirable stresses within the bone material and to accurately and securely attach the bone plate to the bone, it is important that the bores are properly aligned relative to the bone plate and screw receiving apertures, especially when the screw receiving apertures are beveled, shouldered, threaded or otherwise configured to better mate or correspond to a particular bone screw configuration.

While the pilot holes may be drilled by first marking the location of the screw receiving apertures on the bone through the screw-receiving apertures, removing the bone plate and then manually aligning the drill bit with the markings, a better known methodology for creating the screw-receiving pilot holes is to utilize elongated, tubular drill guides that are aligned with the screw receiving apertures. The drill guides may be temporarily attached or mounted to the bone plates to extend proximally from the screw receiving apertures in order to insure proper location and alignment of the pilot hole and bone screw relative to the bone plate. With such an assembly, the bone plate is manually held or temporarily affixed in proper position over the bone or bone segments, the drill bit is inserted into the drill guide so as to extend through the screw receiving aperture to the bone, the pilot hole is created in the bone, the bit is removed from the drill guide, the drill guide is detached from the bone plate, and the bone screw is inserted through the screw receiving aperture and into the pilot hole to secure the bone plate to the bone.

A problem that has been noted with the known systems is that the removal of the drill guide members from the bone plate prior to insertion of the bone screws into the apertures often results in movement of the bone plate relative to the bone or bone segments and the pilot holes that have been created. This may results in misalignment of the bone screws when they are implanted to secure the bone plate to the bone or misplacement of the bone plate.

It is an object of this invention to address this problem by providing a bone plate locking cannula and drill guide assembly, and its method of use, wherein locking cannulas are temporarily attached to the bone plate in proper alignment with the screw-receiving screw receiving apertures, the cannulas being sized to receive a tubular drill guide. The bone plate, screw receiving apertures, bone screws, drill bits, drill guides and locking cannulas of the assembly are sized and structured such that after drilling the pilot bore into the bone and removing the drill bit and drill guide from the locking cannula, the internal diameter of the locking cannula is sufficiently large such that the bone screw may be inserted through the cannula and driven into the bone through the screw receiving aperture to secure the bone plate to the bone without requiring removal of the locking cannula. After the bones screw is fully inserted into the bone, the locking cannula is then removed from the bone plate. These and other objects not expressly set forth in this section will be supported or made obvious based on the following disclosure.

SUMMARY OF THE INVENTION

The invention in various embodiments in general a bone plate locking cannula and drill guide assembly comprising a bone plate and at least one locking cannula member, the bone plate being a rigid body, typically composed of metal, ceramic or hard polymer material, shaped to sufficiently conform for secure attachment to the surface of the bone to be repaired or to provide a framing or base structure to properly align the bone or bone segments during healing, the bone plate having multiple screw-receiving apertures through which bone screws are inserted to fixedly secure the bone plate to the underlying bone or bone segments. An elongated, tubular locking cannula is provided, the locking cannula and bone plate being structured such that the cannula is temporarily mountable to the bone plate utilizing a threaded connection.

The screw receiving apertures are configured to comprise a proximal or exterior bore and a distal or interior bore, the distal bore being smaller in diameter than the proximal bore. The proximal bore is internally threaded to receive an externally threaded end of the locking cannula in order to temporarily secure the locking cannula to the bone plate. The distal bore of the screw receiving apertures may or may not be internally threaded. The bone screws comprise a threaded shaft adapted to be driven into the bone and a screw head to preclude passage of the bone screw completely through the screw receiving aperture. The maximum diameter of the bone screw is smaller than the internal diameter of the bore of the locking cannula. A pilot hole in the bone is created by inserting an elongated, tubular drill guide into the locking cannula, then inserting a twist drill or drill bit into the drill guide and through the screw receiving aperture. The twist drill and drill guide are then removed from the locking cannula and the bone screw is passed through the locking cannula and into the screw receiving aperture, then driven into the bone without requiring removal of the locking cannula from the bone plate.

In order to affix the bone plate to underlying bone or bone segments, the bone plate is positioned at its desired location and the locking cannula is mounted to the bone plate. An elongated drill guide is then inserted into the locking cannula and a twist drill or drill bit is inserted into and through the drill guide and the corresponding screw receiving aperture to create a screw-receiving pilot hole in the bone, the affixed locking cannula insuring that the pilot hole is properly aligned relative to the screw receiving aperture and the bone plate. The drill and drill guide are removed and a bone screw is passed down through the locking cannula and inserted into the screw receiving aperture. An elongated drive tool is inserted into the locking cannula and the bone screw is rotationally driven into the bore to secure the bone plate to the bone. These steps are repeated in successive screw receiving apertures until the bone plate is securely fastened onto the bone.

In addition to an embodiment wherein a single locking cannula is used with each successive screw receiving apertures, in other embodiments all screw-receiving apertures may each be provided with a dedicated locking cannula, while in other embodiments the locking cannulas may be mountable only on selected apertures. The latter embodiment may be necessary when access space is limited. For the latter circumstance, once the bone screws have been properly affixed to the bone in the selected apertures such that the bone plate is secured in proper position on the bone, the locking cannulas are removed. The screw-receiving bores corresponding to the remaining apertures may be created without the use of the locking cannulas. In still another embodiment, selected apertures may be structured to receive the locking cannula, while other apertures on the bone plate may be standard threaded or non-threaded apertures not adapted to receive the locking cannula.

In alternative terms, the invention in various aspects is a bone plate locking cannula assembly comprising a bone plate comprising screw receiving apertures, each said screw receiving aperture comprising an internally threaded proximal bore having a proximal bore internal diameter and a coaxially aligned distal bore having a distal bore internal diameter, said proximal bore internal diameter being greater than said distal bore internal diameter; a locking cannula detachably mounted to one of said screw receiving apertures, said locking cannula having a proximal end, a tubular shaft, a longitudinal bore having a longitudinal bore internal diameter, and a distal end having external threading, said distal end sized and configured to be received by and mate with said internally threaded proximal bores of said screw receiving apertures; and bone screws each comprising an externally threaded shaft and a screw head, said bone screws being sized so as to pass through said locking cannula longitudinal bore, wherein said externally threaded shaft is sized to pass through said distal bores of said screw receiving apertures and said screw head is sized to be precluded from passing through said distal bores of said screw receiving apertures. Furthermore, the invention is such an assembly wherein said distal bores are non-threaded; wherein said distal bores are internally threaded; each of said screw receiving apertures further comprising a transition shoulder between said proximal bore and said distal bore, and wherein said distal end of said locking cannula contacts said transition shoulder when said locking cannula is detachably mounted to said screw receiving apertures; each of said screw receiving apertures further comprising a transition shoulder between said proximal bore and said distal bore, and wherein said screw heads are received within said distal bores and are precluded from passing through said distal bores by said transition shoulder; wherein said externally threaded distal end of said locking cannula defines an abutment shoulder, and wherein said abutment shoulder of said locking cannula contacts said bone plate when said locking cannula is detachably mounted to said screw receiving apertures; wherein said bone plate further comprises conventional screw receiving apertures not adapted to receive said locking cannula; wherein said screw heads are externally threaded so as to be received by said internally threaded distal bores; further comprising a drill guide, said drill guide comprising an elongated tubular shaft and a drill guide longitudinal bore, said tubular shaft having an external diameter smaller than said internal diameter of said locking cannula longitudinal bore such that said tubular shaft is removably received within said locking cannula longitudinal bore; said drill guide longitudinal bore having an internal diameter smaller than said distal bore internal diameter of said screw receiving apertures; further comprising a drill received within said drill guide longitudinal bore, said drill having an external diameter smaller than said internal diameter of said drill guide longitudinal bore; and/or further comprising additional locking cannulas.

In alternative terms, the invention in various aspects is a bone plate locking cannula and drill guide assembly comprising a bone plate comprising screw receiving apertures, each said screw receiving aperture having an internally threaded proximal bore with approximal bore internal diameter and a distal bore with a distal bore internal diameter, said proximal bore and said distal bore being coaxial, said proximal bore internal diameter being greater than said distal bore internal diameter whereby a transition shoulder is disposed between said proximal bore and said distal bore; at least one elongated locking cannula detachably mounted to said screw receiving apertures, said at least one locking cannula having a proximal end, a tubular shaft, a longitudinal bore having an internal diameter, and a distal end having external threading, said externally threaded distal end sized and configured to threadingly mate with said internally threaded proximal bores of said screw receiving apertures to removably mount said at least one locking cannula to said bone plate; at least one drill guide, said at least one drill guide comprising an elongated tubular shaft and a drill guide longitudinal bore having an internal diameter, said tubular shaft having an external diameter smaller than said internal diameter of said locking cannula longitudinal bore such that said tubular shaft is removably received within said locking cannula longitudinal bore; and bone screws each comprising an externally threaded shaft and a screw head having a maximum diameter, said internal diameter of said locking cannula longitudinal bore being greater than said maximum diameter of said screw head, such that said bone screw are passable through said locking cannula longitudinal bore, wherein said externally threaded shaft is sized to pass through said distal bore and said screw head is sized to be precluded from passing through said distal bore by said transition shoulder. Furthermore, the assembly wherein said distal end of said at least one locking cannula contacts said transition shoulder when said at least one locking cannula is detachably mounted to said screw receiving apertures; said externally threaded distal end of said at least one locking cannula defining an abutment shoulder, and wherein said abutment shoulder of said at least one locking cannula contacts said bone plate when said at least one locking cannula is detachably mounted to said screw receiving apertures; wherein said bone plate further comprises conventional screw receiving apertures not adapted to receive said drill guides.

Alternatively, in other aspects, the invention is a method of affixing a bone plate to bone comprising the steps of (a) providing a bone plate locking cannula and drill guide assembly comprising a bone plate comprising screw receiving apertures, each said screw receiving aperture having an internally threaded proximal bore with approximal bore internal diameter and a distal bore with a distal bore internal diameter, said proximal bore and said distal bore being coaxial, said proximal bore internal diameter being greater than said distal bore internal diameter whereby a transition shoulder is disposed between said proximal bore and said distal bore; at least one elongated locking cannula detachably mounted to said screw receiving apertures, said at least one locking cannula having a proximal end, a tubular shaft, a longitudinal bore having an internal diameter, and a distal end having external threading, said externally threaded distal end sized and configured to threadingly mate with said internally threaded proximal bores of said screw receiving apertures to removably mount said at least one locking cannula to said bone plate; at least one drill guide, said at least one drill guide comprising an elongated tubular shaft and a drill guide longitudinal bore having an internal diameter, said tubular shaft having an external diameter smaller than said internal diameter of said locking cannula longitudinal bore such that said tubular shaft is removably received within said locking cannula longitudinal bore; and bone screws each comprising an externally threaded shaft and a screw head having a maximum diameter, said internal diameter of said locking cannula longitudinal bore being greater than said maximum diameter of said screw head, such that said bone screw are passable through said locking cannula longitudinal bore, wherein said externally threaded shaft is sized to pass through said distal bore and said screw head is sized to be precluded from passing through said distal bore by said transition shoulder; (b) positioning said bone plate on a bone; (c) mounting said at least one locking cannula to one of said screw receiving apertures; (d) inserting said drill guide into said locking cannula; (e) providing a drill and inserting said drill into said drill guide and drilling a pilot hole into said bone through said one of said screw receiving apertures; (f) removing said drill and said drill guide from said locking cannula; (g) inserting a bone screw into said locking cannula and driving said bone screw through said one of said screw receiving apertures into said bone; (h) removing said locking cannula from said one of said screw receiving apertures; (i) mounting said at least one locking cannula to another of said screw receiving apertures; and (j) repeating steps (d) through (h). Furthermore, the method wherein said step of providing a bone plate locking cannula and drill guide assembly comprises providing a bone plate having conventional screw receiving apertures not adapted to matingly receive said at least one locking cannula in addition to said screw receiving apertures adapted to matingly receive said at least one locking cannula; and further comprising the step of driving said bone screws directly into bone through said conventional screw receiving apertures; and/or wherein said step of mounting said at least one locking cannula to one of said screw receiving apertures is performed by first inserting said locking cannula through body tissue.

DETAILED DESCRIPTION OF THE INVENTION

Figure 2:
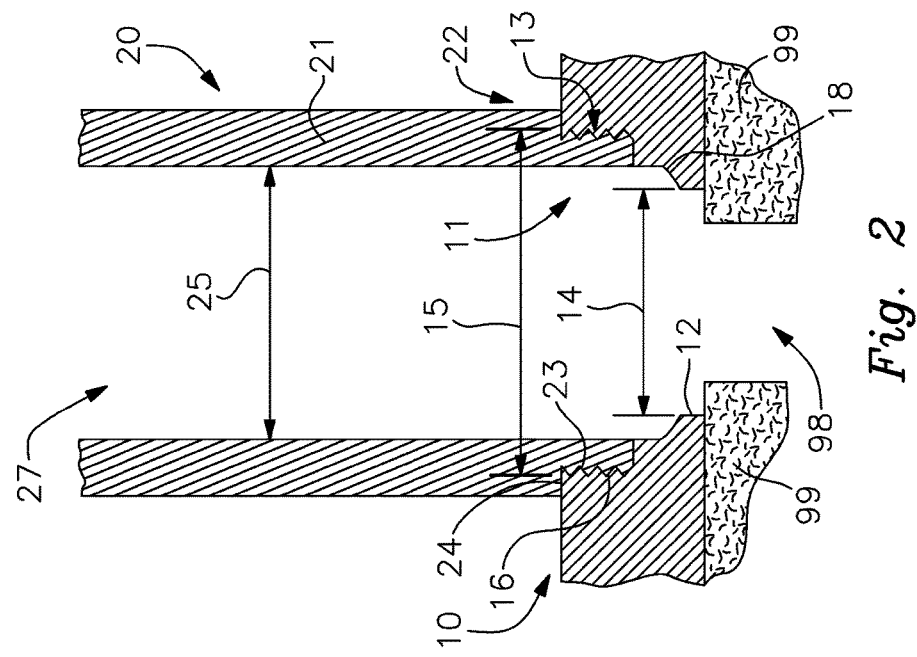
FIG. 2 is a partial cross-sectional view of the embodiment of FIG. 1 showing the locking cannula mounted to the bone plate, the drill and drill guide having been removed from the locking cannula.

With reference to the embodiments shown in the representative drawings, the number of which is not meant to be limiting in terms of the possible embodiments or the scope and definition of the invention, the invention can be considered to comprise in general an assembly comprising a bone plate 10 and a locking cannula 20, as well as its method of use, the bone plate 10 being a rigid member, typically metal, ceramic or had polymer, shaped to conform to the surface of a bone or bone segments 99 to be repaired or alternatively to provide a framework or base for rigid attachment of bone or bone segments 99, the bone plate 10 having multiple screw-receiving apertures 11 through which bone screws 30 are inserted to secure the bone plate 10 to the underlying bone or bone segments 99. The bone plate 10 may be configured and structured to secure a single bone or bone segments 99, or may be configured and structures to connect bones or bone segments 99 to a distractor device or other instrumentation. Elongated, tubular locking cannulas 20 are provided as part of the assembly, the locking cannulas 20 and bone plates 10 being structured such that the locking cannulas 20 are temporarily mountable to the bone plate 10 utilizing a threaded connection. The assembly may further comprise a tubular drill guide 40, the drill guide 40 being sized to so as to coaxially disposed within the locking cannula 20. The drill guide 40 properly orients the drill relative to the screw receiving aperture 11 during creation of a pilot hole 98 to later receive the bone screw 30. The internal diameter 25 of the locking cannula 20 is greater than the maximum diameter 35 of the bone screw 30, such that upon removal of the drill guide 40 from the locking cannula 20, the bone screw 30 may be delivered through the locking cannula 20 and inserted into the bone 99 without requiring removal of the locking cannula from the bone plate 10.

As used herein, terms such as proximal shall refer to the side or direction away from the bone or bone segments 99 to which the bone plate 10 is being affixed, while terms such as distal shall refer to the side or direction toward the bone or bone segments 99 to which the bone plate 10 is being affixed. In terms of the surgeon implanting the bone plate 10, proximal is toward or near to the surgeon and distal is away are farther from the surgeon.

Figure 1:
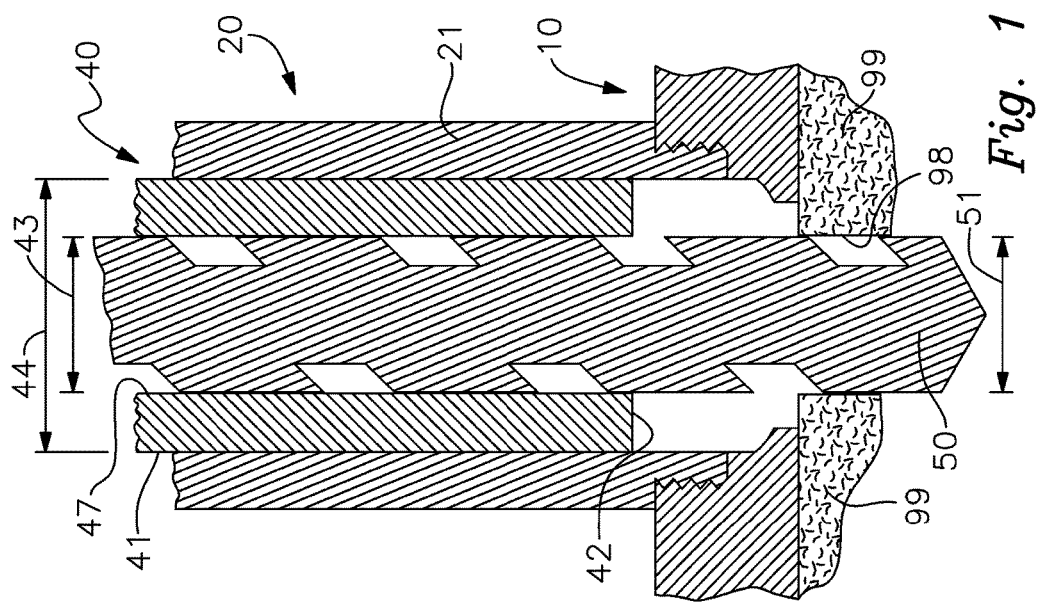
FIG. 1 is a partial cross-sectional view of an embodiment of the invention showing a portion of the bone plate, the screw receiving aperture, the locking cannula mounted to the bone plate, the drill guide inserted within the locking cannula and a drill guided by the drill guide and creating a pilot hole, the distal bore of the screw receiving aperture being non-threaded and comprising a shoulder to receive the screw head.
Figure 5:
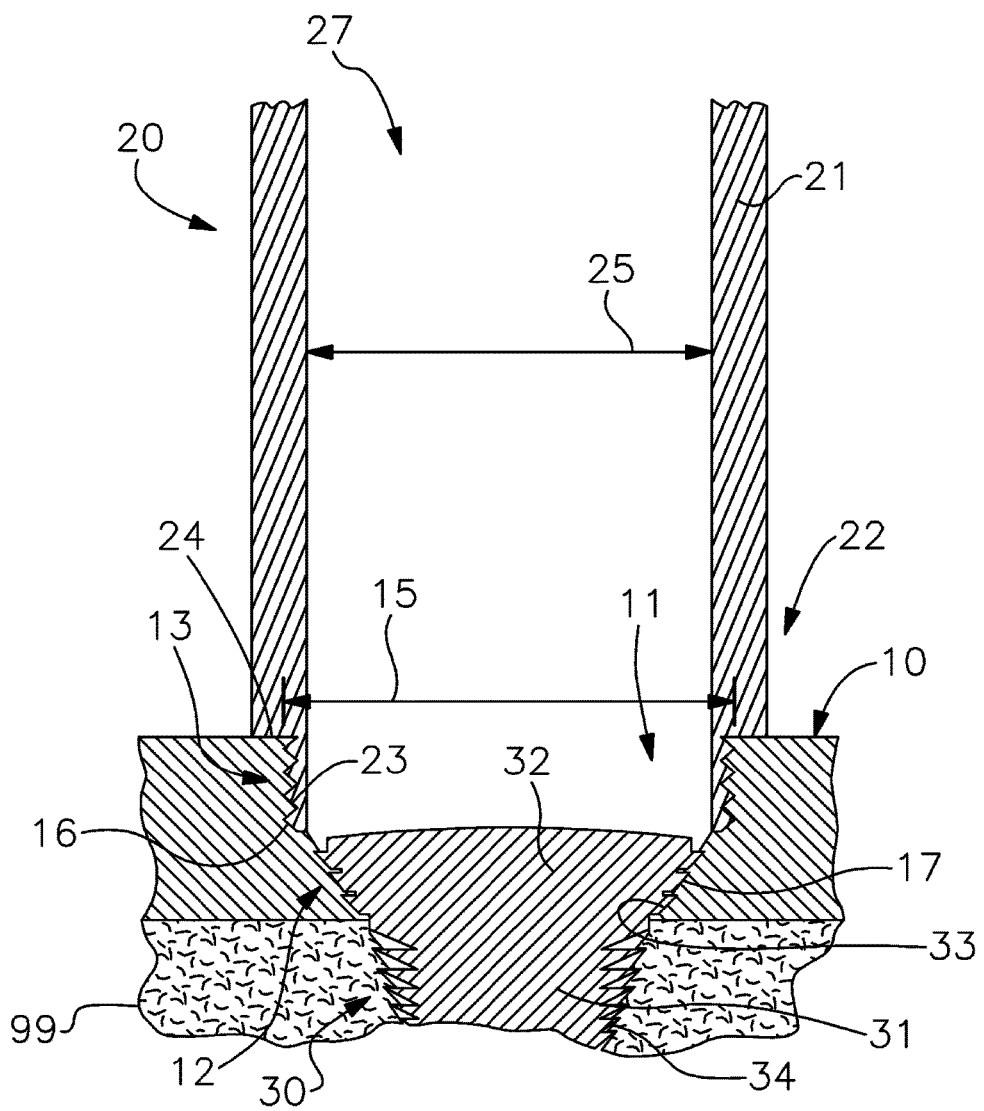
FIG. 5 is a partial cross-sectional view of another embodiment of the invention showing a portion of the bone plate, the screw receiving aperture, the locking cannula and the bone screw inserted into the bone, the distal bore of the screw receiving aperture being internally threaded and receiving the externally threaded portion of the screw head.
Figure 6:
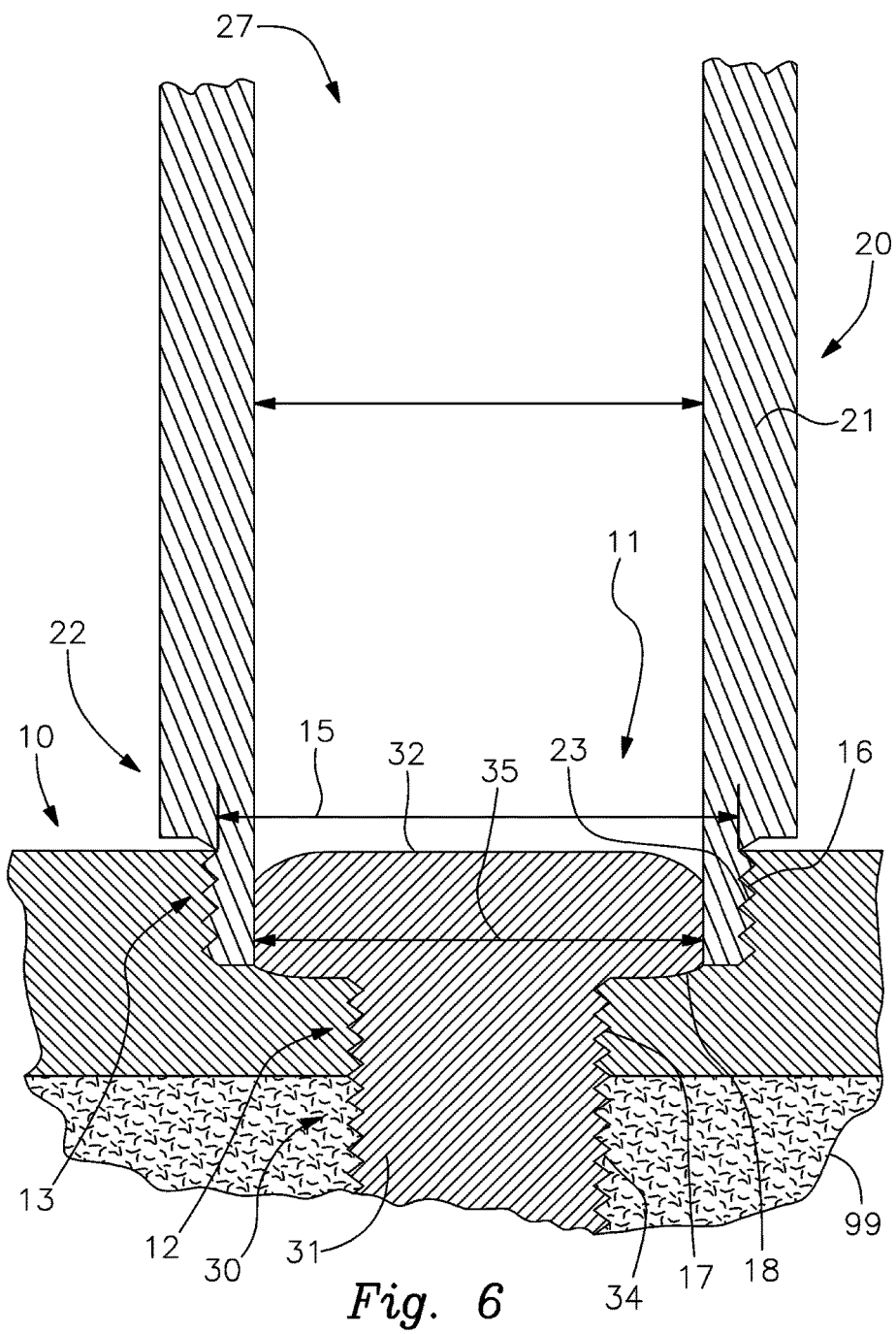
FIG. 6 is a partial cross-sectional view of another embodiment of the invention showing a portion of the bone plate, the screw receiving aperture, the locking cannula and the bone screw inserted into the bone, the distal bore of the screw receiving aperture being internally threaded to receive the externally threaded portion of the bone screw shaft, the diameter of the distal bore being significantly less than the diameter of the proximal bore such that a shoulder is defined to receiver the screw head.

The hollow, longitudinally bored, tubular locking cannula 20 comprised a tubular shaft 21 having a longitudinal bore 27, the locking cannula 20 having a proximal end 26 and a distal end 22. The distal end 22 is provided with external threading 23 adapted to mate with internal threading 16 present in the proximal bore 13 of the bone plate 10. The threaded distal end 22 may be reduced in external diameter relative to the tubular shaft 21 to define an abutment shoulder 24 that functions to stop advancement of the locking cannula 20 into the bone plate 10, as shown in FIGS. 1 and 5, or the connection between the bone plate 10 and the locking cannula 20 may be structured such that the distal end 22 bottoms out on the transition shoulder 18 between the proximal bore 13 and the distal bore 12 of the base plate aperture 11 without the abutment shoulder 24 contacting the base plate 10, as shown in FIG. 6. With this structure the locking cannula 20 may be temporarily yet rigidly mounted onto bone plate 10 and subsequently removed from the bone plate 10 by rotating the locking cannula 20 relative to the bone plate 10, preferably utilizing a handled trocar or other member or mechanism to provide for manual rotation of the locking cannula 20.

The screw receiving apertures 11 are structured to comprise a proximal or exterior bore 13 and a coaxial distal or interior bore 12, the distal bore 12 having an internal diameter 14 lesser than the internal diameter 15 of the proximal bore 13 such that a transition shoulder 18 is formed between the proximal bore 13 and the distal bore 12. The proximal bore 13 comprises internal threading 16 to receive and mate with external threading 23 disposed on the distal end 22 of the locking cannula 20. The distal bore 20 may or may not be internally threaded. The embodiment of FIG. 1 shows a non-threaded distal bore 20 while the embodiments of FIGS. 5 and 6 show threaded distal bores 20. In the embodiment of FIG. 5, the distal bore 20 is tapered in the distal direction, with the internal diameter 14 as used herein being defined as the maximum diameter of the distal bore 20. The provision of a larger proximal bore 13 and a smaller distal bore 12 is desirable as with this structure the screw head 32 is received in a recessed manner and does not significantly protrude above the exterior or proximal surface of the bone plate 10 once implanted. Most preferably the depth of the proximal bore 13 is equal to or greater than the depth of the screw head 32, such that no portion of the screw head 32 extends above the exterior surface of the bone plate 10 once the bone screw 30 is fully inserted.

The bone screws 30 each comprise a threaded shaft 31 with external threading 34, adapted to extend through the bone plate 10 to be received by the bone 99, and a larger screw head 32, preferably circular to define a maximum diameter 35 adapted to preclude passage of the bone screw 30 completely through the bone plate 10. The screw head 32 is structured in known manner, e.g., slotted or provided with a non-circular recess, to receive the end of a drive tool, e.g., a screwdriver. The maximum diameter 35 of the screw head 32, and any portion of the bone screw 30, is smaller than the internal diameter 25 of the locking cannula bore 27, such that the bone screw 30 may be inserted through the proximal end 26 down through tubular shaft 21 and past the distal end 22 of the locking cannula 20 such that the threaded shaft 31 extends into and through the screw receiving aperture 11, whereupon it may be driven into the bone 99. In this manner the threaded shaft 31 extends through the screw receiving aperture 11 into the bone 99, while the transition shoulder 18 between the proximal bore 13 and the distal bore 12 defines a stop against further advancement of the screw head 32, the screw head maximum diameter 35 being greater than the distal bore diameter 14. The screw head 32 may be provided with no threading, as shown in FIGS. 1 and 6, or may be provided with external threading 33, as shown in FIG. 5.

Figure 7:
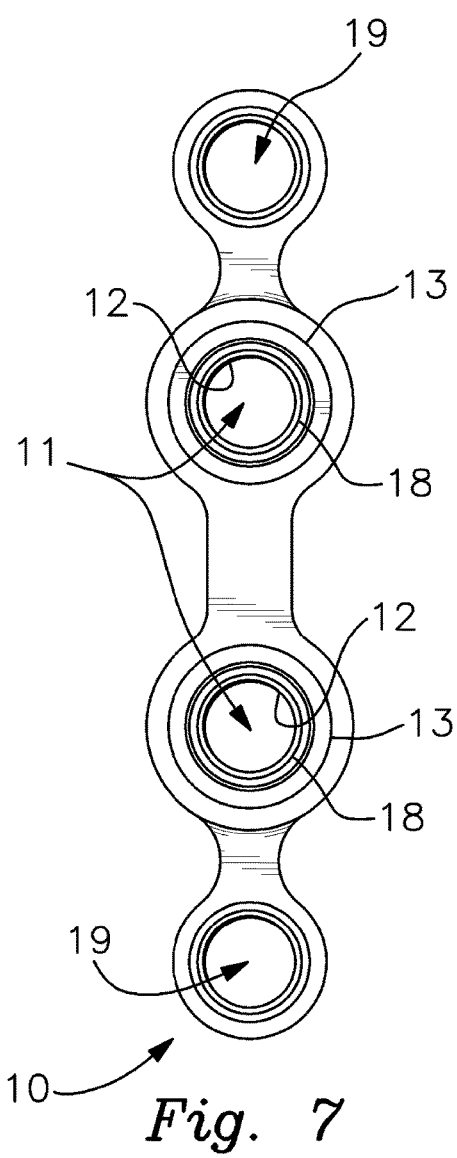
FIG. 7 is a plan view of the proximal side of a representative embodiment of a bone plate.
Figure 8:
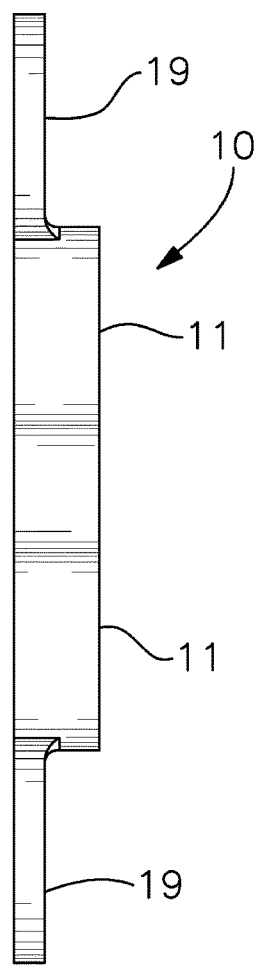
FIG. 8 is a side view of the bone plate embodiment of FIG. 7.
Figure 9:
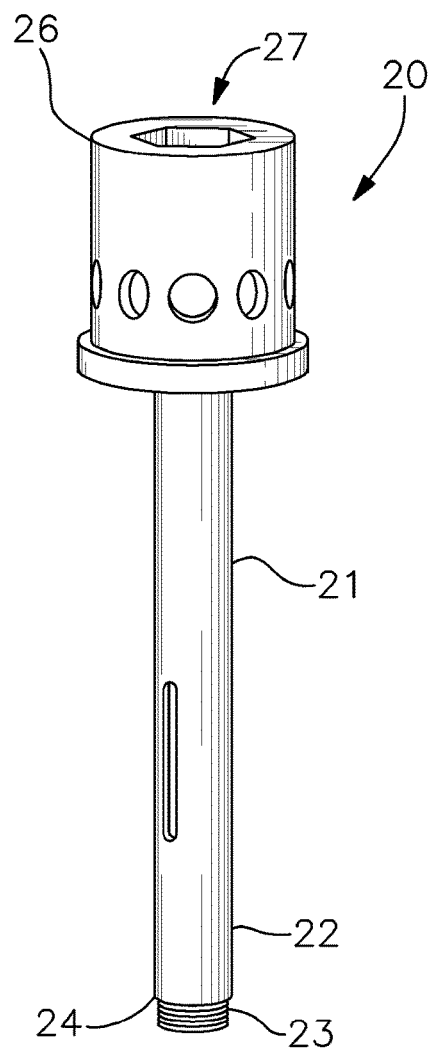
FIG. 9 is a view of a representative embodiment of a locking cannula.

All of the apertures 11 of the bone plate 10 may be structured to temporarily receive the locking cannulas 20. Alternatively, as illustrated in FIGS. 7 and 8, the bone plate 10 may be provided with some apertures 11 capable of receiving the drill guides and other conventional screw receiving apertures 19, either threaded or non-threaded, through which bone screws 30 may be driven, such conventional apertures 19 lacking the proximal bore/distal bore structure required for mounting the locking cannula 20 to the bone plate 10.

Figure 10:
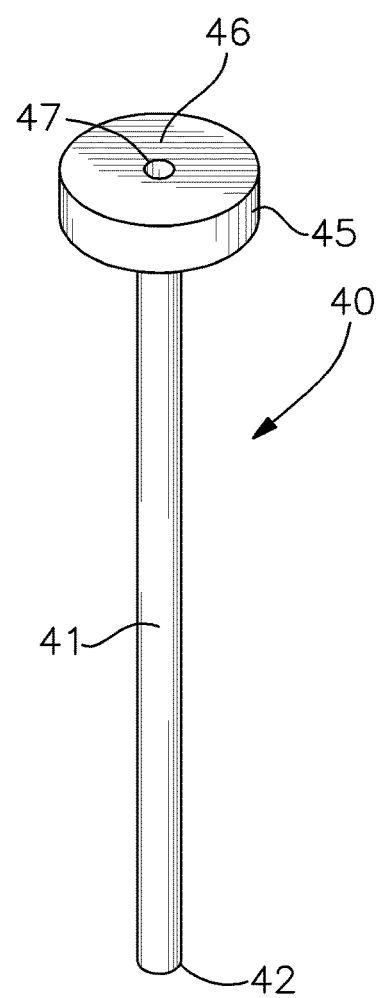
FIG. 10 is a view of a representative embodiment of a drill guide.

In certain embodiments the assembly further comprises an elongated, hollow drill guide 40 having an elongated tubular shaft 41, a distal end 42, a proximal end 46, a longitudinal bore 47 and a handle 45. The tubular shaft 41 has an external diameter 44 and the longitudinal bore 47 has an internal diameter 44. A representative drill guide 40 is shown in FIGS. 1 and 10. The drill guide external diameter 44 is smaller than the internal diameter 25 of the locking cannula longitudinal bore 27, such that the drill guide tubular shaft 41 is coaxially insertable into the locking cannula longitudinal bore 27, as shown in FIG. 1. The drill guide internal diameter 43 is smaller than the distal bore diameter 14 of the bone plate 10. The assembly may further comprise a drill or drill bit 50, such as a manual twist drill for example, wherein the external diameter 51 of the drill 50 is smaller than the drill guide internal diameter 43 and smaller than the distal bore diameter 14 of the bone plate 10, as seen in FIG. 1. The drill 50 is utilized to create a pilot bore or hole 98 to receive a bone screw threaded shaft 31 in normal manner.

In one embodiment of the method, such as for a transbuccal implantation for example, the bone plate 10 is positioned against the bone 99 at the desired attachment location. The distal end 22 of the tubular shaft 21 of the locking cannula 20 is inserted through a small incision or puncture in the cheek tissue in known manner, typically with a trocar inserted into the longitudinal bore 27 to occlude the longitudinal bore 27 during insertion. The locking cannula 20 is aligned with the proximal bore 13 of one of the screw receiving apertures 11 and axially rotated such that the locking cannula external threading 23 mates with the proximal bore internal threading 16, thereby properly coaxially aligning and orienting the axis of the locking cannula 20 to the axis of the proximal bore 13 and the shared axis of the distal bore 12. The trocar is removed and the drill guide 40 is inserted into the locking cannula 20 such that the axis of the drill guide longitudinal bore 47 is coaxially aligned with the axis of the locking cannula longitudinal bore 27. The drill 50 is then inserted into the drill guide 40 and a centered, coaxially aligned pilot hole 98 is created in the bone 99, as shown in FIG. 1.

Figure 3:
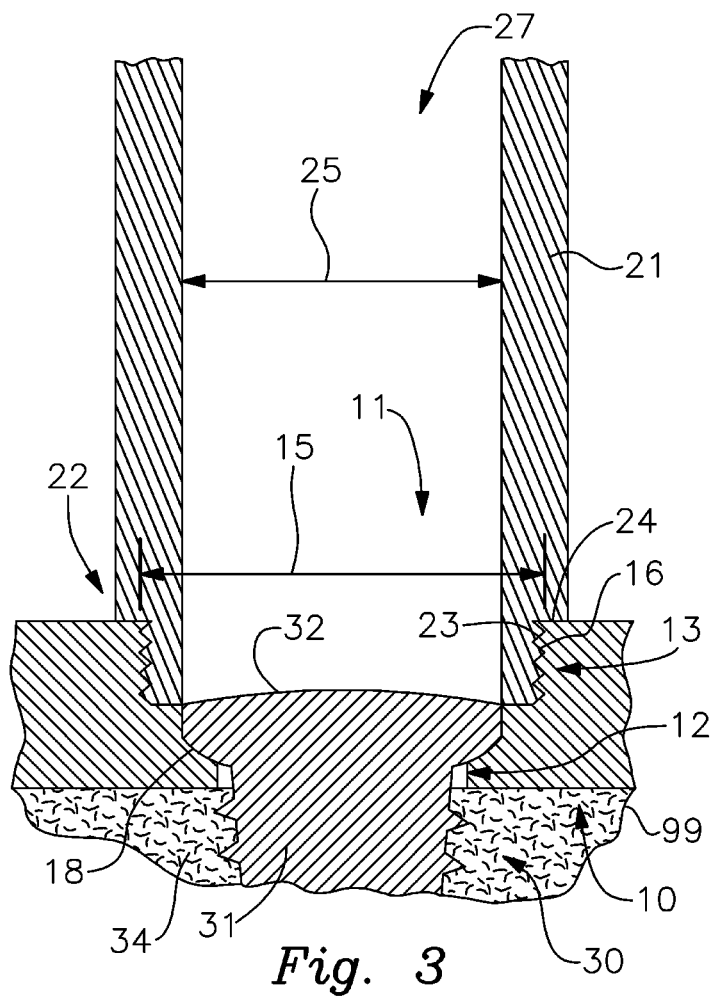
FIG. 3 is a partial cross-sectional view of the embodiment of FIG. 1 showing the bone screw fully inserted into the screw receiving aperture prior to removal of the locking cannula from the bone plate.
Figure 4:
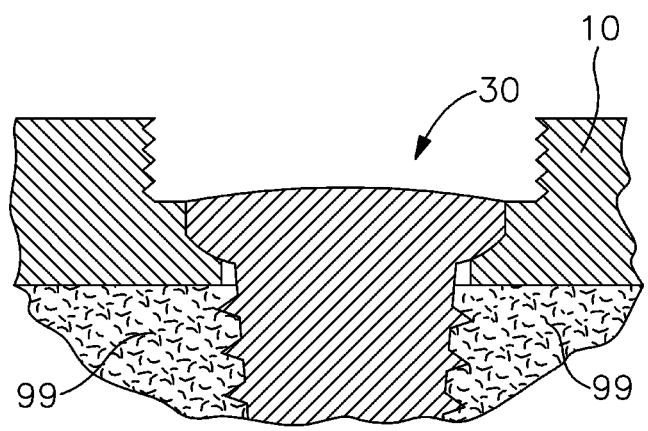
FIG. 4 is a partial cross-sectional view of the embodiment of FIG. 1 showing the bone screw fully inserted into the screw receiving aperture after removal of the locking cannula from the bone plate.

The drill 50 and the drill guide 40 are then removed from the locking cannula 20, as shown in FIG. 2. Because the internal diameter 25 of the locking cannula internal bore 27 is greater than the external diameter 44 of the bone screw 30, the bone screw is inserted into the proximal end 26 of the locking cannula 20 and guided or funneled to the screw receiving aperture 11. Utilizing a drive tool, not shown, the externally threaded shaft 31 of the bone screw 30 is maneuvered through the aperture 11 and into the pilot hole 98, then rotated in known manner such that the bone screw 30 advances into the bone 99. As the bone screw 30 is advanced the distal side of the screw head 32 abuts the abutment shoulder 24 between the wider proximal bore 13 and the narrower distal bore 12 of the screw receiving aperture 11, such that the plate 10 is affixed securely on the bone 99, as shown in FIG. 3. The presence of the locking cannula 20 further insures that the bone screw 30 is properly oriented into the bone 99 relative to the bone palte aperture 11. With the bone screw 30 fully inserted, the locking cannula 20 is now rotated and removed from the bone plate 10. For implantation of subsequent bone screws 30 the process is then repeated from the step of inserting the locking cannula 20 through the cheek forward. The description of a transbuccal implantation is not meant to be limiting, as the assembly and its methodology may be utilized at other locations.

In an alternate method embodiment in circumstances where the attachment zone for the bone plate 10 is adequately exposed, plural locking cannulas 20 are mounted to some or all of the screw receiving apertures 10 on the bone plate 10 and the bone plate 10 is positioned at the proper location on the bone or bone segments 99. The bone screws 30 are then inserted into the bone 99 as set forth above and with the bone plate 30 properly secured to the bone 99, the locking cannulas 20 are removed from the bone plate 10. In still another alternate method embodiment, wherein some of the screw receiving apertures 11 are covered by body tissue and other apertures 19 are externally exposed, the locking cannulas 20 may be utilized for the covered apertures 11 in the manner set forth above and bone screws 30 may be inserted in direct manner into the conventional screw receiving apertures 19, the conventional screw receiving apertures 19 not having any internal threading.

The embodiments discussed and illustrated are not meant to be limiting, and it is understood and contemplated that equivalents and substitutions for some elements set forth above may be obvious to those of skill in the art, and therefore the true scope and definition of the invention is to be as set forth in the following claims.

We claim:

1. A bone plate locking cannula assembly comprising:
   a bone plate comprising screw receiving apertures, each said screw receiving aperture comprising an internally threaded proximal bore having a proximal bore internal diameter and a coaxially aligned distal bore having a distal bore internal diameter, said proximal bore internal diameter being greater than said distal bore internal diameter;
   a locking cannula detachably mounted to one of said screw receiving apertures, said locking cannula having a proximal end, a tubular shaft, a longitudinal bore having a longitudinal bore internal diameter, and a distal end having external threading, said distal end sized and configured to be received by and mate with said internally threaded proximal bores of said screw receiving apertures;
   a drill guide, said drill guide comprising an elongated tubular shaft and a drill guide longitudinal bore, said tubular shaft having an external diameter smaller than said internal diameter of said locking cannula longitudinal bore such that said tubular shaft is removably received within said locking cannula longitudinal bore; and
   bone screws each comprising an externally threaded shaft and a screw head, said screw heads of said bone screws being sized so as to pass completely through said locking cannula longitudinal bore and said locking cannula distal end, wherein said externally threaded shaft is sized to pass through said distal bores of said screw receiving apertures and said screw head is sized to be precluded from passing through said distal bores of said screw receiving apertures.

2. The assembly of claim 1, wherein said distal bores are non-threaded.

3. The assembly of claim 1, wherein said distal bores are internally threaded.

4. The assembly of claim 3, wherein said screw heads are externally threaded so as to be received by said internally threaded distal bores.

5. The assembly of claim 1, each of said screw receiving apertures further comprising a transition shoulder between said proximal bore and said distal bore, and wherein said distal end of said locking cannula contacts said transition shoulder when said locking cannula is detachably mounted to said screw receiving apertures.

6. The assembly of claim 1, each of said screw receiving apertures further comprising a transition shoulder between said proximal bore and said distal bore, and wherein said screw heads are received within said distal bores and are precluded from passing through said distal bores by said transition shoulder.

7. The assembly of claim 1, wherein said externally threaded distal end of said locking cannula defines an abutment shoulder, and wherein said abutment shoulder of said locking cannula contacts said bone plate when said locking cannula is detachably mounted to said screw receiving apertures.

8. The assembly of claim 1, wherein said bone plate further comprises conventional screw receiving apertures not adapted to receive said locking cannula.

9. The assembly of claim 1, said drill guide longitudinal bore having an internal diameter smaller than said distal bore internal diameter of said screw receiving apertures.

10. The assembly of claim 9, further comprising a drill received within said drill guide longitudinal bore, said drill having an external diameter smaller than said internal diameter of said drill guide longitudinal bore.

11. The assembly of claim 1, further comprising additional locking cannulas.

12. A bone plate locking cannula and drill guide assembly comprising:
    a bone plate comprising screw receiving apertures, each said screw receiving aperture having an internally threaded proximal bore with a proximal bore internal diameter and a distal bore with a distal bore internal diameter, said proximal bore and said distal bore being coaxial, said proximal bore internal diameter being greater than said distal bore internal diameter whereby a transition shoulder is disposed between said proximal bore and said distal bore;
    at least one elongated locking cannula detachably mounted to said screw receiving apertures, said at least one locking cannula having a proximal end, a tubular shaft, a longitudinal bore having an internal diameter, and a distal end having external threading, said externally threaded distal end sized and configured to threadingly mate with said internally threaded proximal bores of said screw receiving apertures to removably mount said at least one locking cannula to said bone plate;

at least one drill guide, said at least one drill guide comprising an elongated tubular shaft and a drill guide longitudinal bore having an internal diameter, said tubular shaft having an external diameter smaller than said internal diameter of said locking cannula longitudinal bore such that said tubular shaft is removably received within said locking cannula longitudinal bore; and bone screws each comprising an externally threaded shaft and a screw head having a maximum diameter, said internal diameter of said locking cannula longitudinal bore being greater than said maximum diameter of said screw head, such that said screw heads of said bone screws are sized so as to pass completely through said locking cannula longitudinal bore and said locking cannula distal end, wherein said externally threaded shaft is sized to pass through said distal bore of said screw receiving aperture and said screw head is sized to be precluded from passing through said distal bore by said transition shoulder of said screw receiving aperture.

13. The assembly of claim 12, wherein said distal end of said at least one locking cannula contacts said transition shoulder when said at least one locking cannula is detachably mounted to said screw receiving apertures.

14. The assembly of claim 12, said externally threaded distal end of said at least one locking cannula defining an abutment shoulder, and wherein said abutment shoulder of said at least one locking cannula contacts said bone plate when said at least one locking cannula is detachably mounted to said screw receiving apertures.

15. The assembly of claim 12, wherein said bone plate further comprises conventional screw receiving apertures not adapted to receive said drill guides.

* * * * *